United States Patent [19]

Tunc

[11] 3,939,836

[45] *Feb. 24, 1976

[54] WATER DISPERSIBLE NONWOVEN FABRIC

[75] Inventor: Deger C. Tunc, East Brunswick, N.J.

[73] Assignee: Johnson & Johnson, New Brunswick, N.J.

[ * ] Notice: The portion of the term of this patent subsequent to Apr. 16, 1991, has been disclaimed.

[22] Filed: Feb. 7, 1974

[21] Appl. No.: 440,427

[52] U.S. Cl......... 128/284; 128/290 R; 128/290 W; 128/296; 428/198; 428/245; 428/247; 428/248
[51] Int. Cl.² ................ A61F 13/16; A61F 13/18; A61F 13/20; A41B 13/02
[58] Field of Search........... 128/290 R, 290 W, 284, 128/286, 287; 161/59, 88, 143, 146, 148, 156; 260/227; 117/140; 428/245, 247, 248, 255, 264, 265, 198

[56] References Cited
UNITED STATES PATENTS

| | | | |
|---|---|---|---|
| 3,480,016 | 11/1969 | Costanza | 128/284 |
| 3,521,638 | 7/1970 | Parrish | 128/284 |
| 3,554,788 | 1/1971 | Fechillas | 117/140 |
| 3,580,253 | 5/1971 | Bernardin | 128/290 W |
| 3,610,245 | 10/1971 | Bernardin | 128/290 W |
| 3,804,092 | 4/1974 | Tunc | 128/290 W X |
| 3,828,783 | 8/1974 | Kennette | 128/290 W X |

*Primary Examiner*—George F. Lesmes
*Assistant Examiner*—Alan T. McDonald
*Attorney, Agent, or Firm*—Lawrence D. Schuler

[57] ABSTRACT

A water dispersible nonwoven fabric comprising one or more layers of overlapping, intersecting fibers and from about 4 percent to about 35 percent by weight of a binder comprising an alkali salt of a sulfated cellulose ester, said nonwoven fabric having good tensile strength and abrasion resistance in the presence of body fluids such as urine, blood, and menstrual fluid. The nonwoven fabrics may be incorporated in body fluid absorbent products such as sanitary napkins, diapers, surgical dressings, tampons, nursing pads and the like.

20 Claims, 5 Drawing Figures

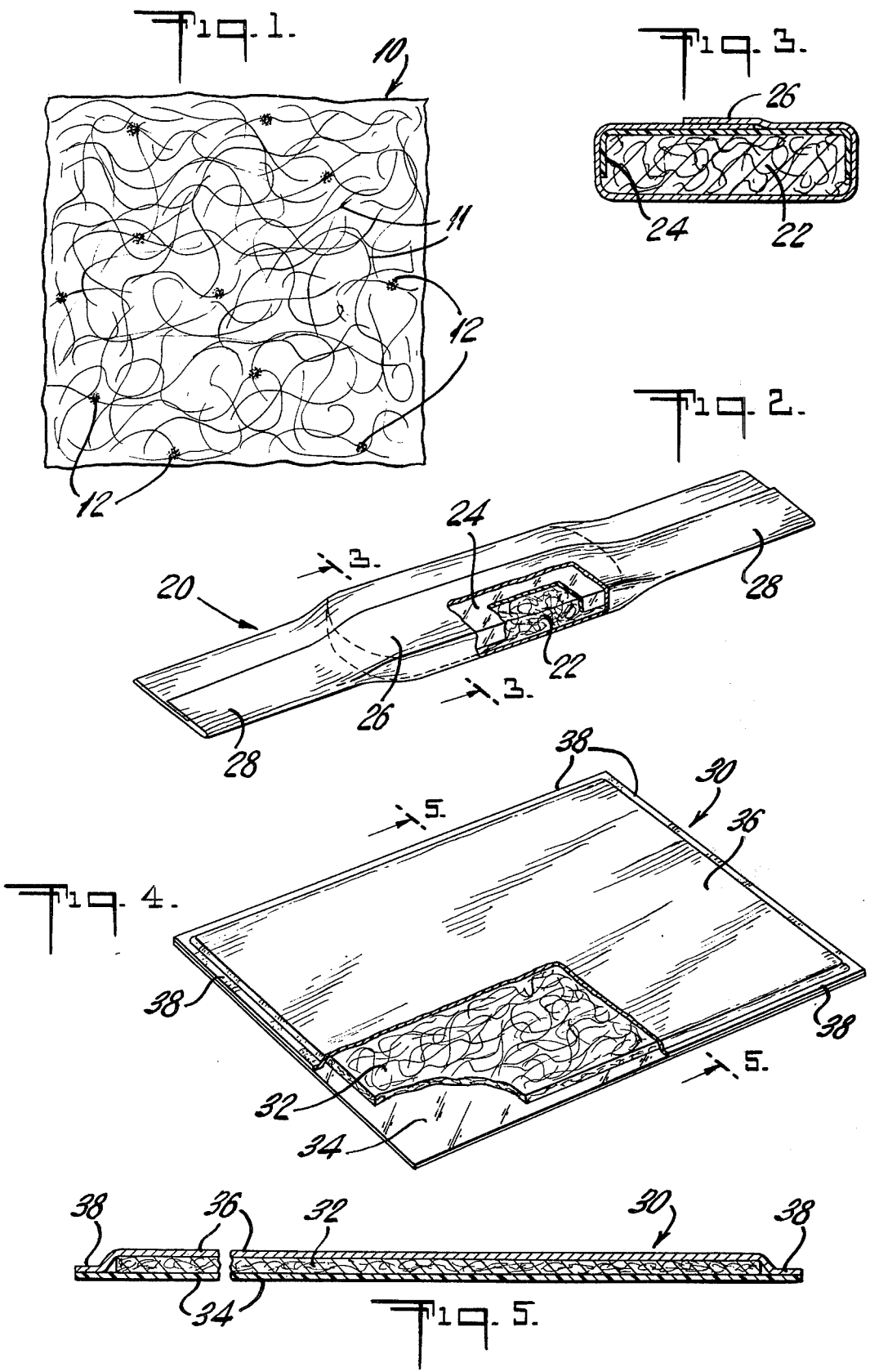

WATER DISPERSIBLE NONWOVEN FABRIC

This invention relates to new nonwoven fabrics which are readily dispersible in water and are flushable. More particularly, this invention relates to nonwoven fabrics which, in addition to having the above-mentioned desirable characteristics, exhibit satisfactory tensile strength when they are contacted with body fluids.

Nonwoven fabrics are widely used as components of such disposable goods as sanitary napkins, diapers, wound dressings, bandages, nursing pads and the like. Such fabrics, if they are to function effectively, must maintain their structural integrity, as well as exhibit satifactory tensile strength, when they are wet or damp with the various body fluids, for example, blood, menstrual fluid, milk and urine, with which they come into contact during use. It has been recognized that if such nonwoven fabrics, while retaining their strength in body fluids, were to lose substantially all their tensile strength when exposed to water and become readily dispersible therein, disposal problems would be substantially eliminated since the fabrics could be easily and conveniently flushed away in a water closet.

Unfortunately, in an attempt to provide nonwoven fabrics having certain in-use characteristics, prior methods have rendered the fabric nondispersible in water. For example, nonwovens have been bonded with body fluid-insoluble resins which impart in-use strength. Generally, however, such resins have also been water insoluble as well and have impeded flushing of the fabric. Therefore, less desirable methods of disposal such as incineration or dumping must be employed.

SUMMARY OF INVENTION

I have now discovered a bonded nonwoven fabric which, in addition to having good strength when dry, and satisfactory strength and abrasion resistance in the presence of most body fluids, such as urine, blood, menstural fluid and the like, is easily dispersible in water and hence is flushable in home water closets and capable of disposal in standard sewer systems or septic systems. In this connection when an article, for example, a barrier means, an absorbent core, a nonwoven fabric or the like is referred to herein as being flushable, it is meant that that article may be deposited in, and flushed through, a water closet without any undue clogging of the water closet or its auxiliary piping. When such an article is referred to herein as being water dispersible, it is meant that that article, when placed in water, loses its integrity and is flushable.

The improved nonwoven fabric of this invention comprises one or more layers of overlapping, intersecting fibers and from about 4 percent to about 35 percent by weight of the fabric of binder. The binder comprises an alkali salt of a sulfated cellulose ester resin, such as, for example, sodium, potassium, or lithium cellulose acetate sulfate; sodium, potassium or lithium cellulose acetate-butyrate sulfate; potassium cellulose butyrate sulfate; and sodium cellulose propionate sulfate. Most preferably the resin binder used in the present invention comprises sodium cellulose acetate sulfate. If so desired, the binder may comprise mixtures of the various alkali cellulose ester sulfates.

The fabrics prepared in accordance with this invention have good dry tensile strength depending upon, among other things, the amount of binder applied to the fabric and the manner in which it is applied. They are abrasion resistant and retain a significant part of their dry tensile strength in solutions containing about 0.8% or more by weight of sodium chloride, and yet are readily dispersible in water. Because of this latter property, the nonwoven fabrics of this invention are uniquely suited for use in products to be contacted with such body fluids as blood, menstrual fluid, urine and the like. These fluids, in general, exhibit properties which, with respect to the binder, are analogous to aqueous salt solutions having a salt content which varies from about 0.8% to about 2.0% by weight of sodium chloride. On the other hand tap water normally supplied to water closets and the like generally has an extremely low concentration of salt, as indicated by a chloride ion cencentration of less than 250 parts per million. It has been discovered that the nonwoven fabrics made as described herein maintain their integrity for a substantial period of time in solutions having a salt concentration exhibiting the properties of body fluids whereas they display a far lower resistance to dispersion in tap water. This unique property is a function of the degree of sulfate substitution which expresses the average number of sulfate groups per anhydroglucose unit of the cellulosic ester. The nonwoven fabric bonded by the aforementioned cellulosic resins will exhibit increasing dispersibility in water and decreasing strength in salt solutions as the degree of sulfate substitution of the cellulosic resin is increased. It has been discovered that a nonwoven fabric bonded by resins having a degree of sulfate substitution varying from about 0.10 to about 0.45 is useful in products designed to be contacted by various body fluids. In another aspect of this invention, the nonwoven fabrics are incorporated into such body fluid absorbent products as sanitary napkins, diapers, surgical dressings, nursing pads, and the like. These products generally include an absorbent core, comprising one or more layers of an absorbent fibrous material. The core may also comprise one or more layers of a fluid-pervious element, such as tissue, gauze, plastic netting, etc. These are generally useful as wrapping materials to hold the components of the core together. Additionally, the core may comprise a fluid-impervious element or barrier means to preclude the passage of fluid through the core and on to its outer surfaces. In accordance with this aspect of the instant invention, a body fluid absorbent product is provided having a nonwoven fabric in contact with an absorbent core, the nonwoven fabric comprising a layer of overlapping intersecting fibers and from about 4 to about 35 percent by weight of the fabric of a binder comprising an alkali salt of a sulfated cellulose ester having an average of from about 0.10 to about 0.45 sulfate groups per anhydroglucose unit.

The invention will be more clearly understood by reference to the attached drawings taken together with the following description.

BRIEF DESCRIPTION OF THE DRAWINGS

FIG. 1 is a plan view of a bonded nonwoven fabric in accordance with the present invention;

FIG. 2 is a perspective view of a sanitary napkin embodying this invention with parts broken away to show the interior construction thereof;

FIG. 3 is a cross-sectional view taken approximately along lines 3—3 of FIG. 2;

FIG. 4 is a perspective view of a disposable diaper embodying this invention with parts broken away to show the interior construction thereof; and FIG. 5 is a cross-sectional view taken approximately along lines 5—5 of FIG. 4.

DETAILED DESCRIPTION OF THE INVENTION

Referring to FIG. 1, there is shown a water dispersible nonwoven fabric 10. The fabric comprises a layer of overlapping, intersecting fibers 11 having substantially uniformly distributed therein a binder comprising an alkali salt of a sulfated cellulose ester 12 as hereinafter described.

The sulfated cellulose esters used to form the binders of this invention may be produced by first forming the sulfate derivative of cellulose and then esterifying with a suitable acylating agent.

The sulfated cellulose is prepared by slurrying cellulose, for example in the form of woodpulp, in an inert liquid reaction medium such as glacial acetic acid and reacting the cellulose slurry with a sulfating mixture prepared from reactants comprising acetic anhydride, an alkali sulfate, glacial acetic acid and sulfuric acid. The sulfated cellulose so obtained is reacted with an acylating agent such as acetic anhydride to form a solution of the desired alkali salt of the sulfated cellulose ester in the reaction mixture. The cellulose ester sulfate is then precipitated from solution by adding the reaction mixture in which it is dissolved to an aqueous precipitation medium maintained at a pH of from about 3 to about 8. The pH of the aqueous precipitation medium is maintained within the specified range by the addition, as necessary, of suitable amounts of an aqueous base. Examples of suitable bases are the alkali metal hydroxides such as sodium, potassium or lithium hydroxide; the salts of alkali metal hydroxides with weak acids, such as sodium carbonate, potassium carbonate, and lithium acetate; and ammonium hydroxide.

Alternatively, solutions of alkali salts of sulfated cellulose esters may be prepared by dissolving a commercially available cellulose ester in an inert liquid reaction medium and then sulfating the cellulose ester with alkali acetyl sulfate, or by other well known procedures. The alkali cellulose ester sulfate may then be recovered by recipitation in an aqueous precipitating medium in the manner described above.

In accordance with this invention, it has been discovered that by modifying the degree of sulfate substitution of the cellulosic resin binder, the salt resistance and water dispersibility of the bonded nonwoven fabric can be modified to provide fabrics which will function effectively when contacted by various body fluids and which may be flushed away in a water closet. Specifically, by lowering the degree of sulfation of the cellulosic resins, the fabrics of this invention become more resistant to salt solutions in that they retain their integrity after being subjected to these solutions for longer periods of time and in that they exhibit higher tensile strengths when subjected to a given salt concentration for a given period of time. In general, if the degree of sulfate substitution of the cellulosic resin is maintained at below about 0.45, an adequately salt resistant nonwoven fabric results. Preferably, the degree of sulfate substitution should be maintained at below about 0.40. While the resistance of the nonwoven fabrics to salt solutions having a salt concentration exhibiting the properties of body fluids increases greatly with decreasing sulfate substitution, the ability of the fabrics to disperse readily in water is maintained until extremely low sulfate substitutions are reached. Adequate water dispersibility is achieved when the degree of sulfate substitution of the cellulosic resin is maintained at a value of at least about 0.10. Preferably, the degree of sulfate substitution should be at least about 0.15, and more preferably, at least about 0.27.

The aforementioned alkali salts of sulfated cellulose esters are used to bond a base layer of fibers to provide the nonwoven fabric of this invention. Suitable base layers comprise most of the well-known fibers, the choice depending upon, for example, fiber cost and the intended end use of the finished fabric. For instance, the base layer may include natural fibers such as cotton, linen, jute, hemp, cotton linters, wool, wood pulp, etc. SImilarly, regenerated cellulosic fibers such as viscose rayon and cuprammonium rayon, modified cellulosic fibers, such as cellulose acetate, or synthetic fibers such as those derived from polyvinyl alcohol, polyesters, polyamides, polyacrylics, etc., alone or in combination with one another, may likewise be used. Natural fibers may be blended with regenerated, modified, and/or synthetic fibers if so desired.

The length of the fiber is important in producing the fabrics of the present invention. The minimum length of the fibers depends on the method selected for forming the base layer. For example, where the base layer is formed by carding, the length of the fiber should usually be a minimum of one-half inch in order to insure uniformity. Where the base layer is formed by air deposition or water deposition techniques, the minimum fiber length may be about 0.05 inch. It has been found that when a substantial quantity of fibers having a length greater than about 2 inches is placed in the fabric, though the fibers will disperse and separate in water, their length tends to form "ropes" of fibers which are undesirable when flushing in home water closets. It is preferred that the fiber length be about 1½ inches or less so that the fibers will not "rope" when they are flushed through a toilet.

The base layers suitable for conversion into the fabric of the present invention may be formed by carding, garnetting, air deposition, water deposition, or any of the other various techniques known in the art. The fibers in the layer may be oriented predominantly in one direction as in a card web or a card web laminate or they may be randomly oriented as in a layer formed by air deposition techniques. For sanitary napkin coverings, disposable diaper facings and similar uses where the fabric is to be flushable, the web is fairly thin and should weigh between 150 to 400 grains per square yard. Where the fabric must possess a substantial amount of strength, uniform fiber distribution is important so as to avoid weak spots in the final nonwoven fabric. Uniform base layers may be produced by carding in which case it is advantageous to use fibers which have good carding characteristics and can be blended into a uniform carded wed with facility. Fibers of viscose rayon and cotton are both satisfactory in this respect.

The amount of sulfated cellulose ester binder distributed in the base layer should be from about 4 to about 35 percent by weight of the final nonwoven fabric. If less than about 4 percent of the cellulosic binder is employed, the fabric does not have sufficient strength and abrasion resistance to be of any utility. If more than about 35 percent of the cellulosic binder is employed, the fabric may lose desirable properties such as absorbency and softness.

It is preferred that the amount of sulfated cellulose ester binder be between about 10 to about 30 percent by weight of the final nonwoven fabric in order to ensure an optimum balance of water dispersibility and wet tensile strength in the presence of various body fluids.

The binder may be distributed in the base layer by printing, spraying, impregnating or by any other technique wherein the amount of binder may be metered and the binder can be distributed uniformly within the base layer. The binder may be distributed throughout the entire base layer or it may be distributed therein in a multiplicity of small closely spaced areas. The binder may be distributed in lines running across, or at an angle to, the width of the web or in separate small shaped areas having circular, angular, square, or triangular configurations. It is preferred that when the binder is applied to the fibrous layer there be left unbonded areas in the layer.

For ease of application to the base fibrous layer, the cellulosic resin binder may be dissolved in water; mixtures of water with acetone, methyl ethyl ketone or methylene chloride; or mixtures of methanol with acetone, methyl ethyl ketone or methylene chloride, to provide solutions containing up to about 30 percent by weight of binder solids. Plasticizers, such as glycerol, polyethylene glycol, and castor oil, may be added to the solution of the cellulosic resin, the amount of such plasticizers varying according to the softness required in the final fabric. Perfumes, coloring agents, antifoams, bactericides, surface active agents, thickening agents and similar additives may be incorporated into the solution of the cellulosic resin binder if so desired. Other binding agents such as polyvinyl alcohol or aqueous dispersions of, for example, polyvinyl chloride, polyvinyl acetate, polyacrylates, polymethacrylates, copolymers of acrylates and methacrylates, copolymers of vinyl acetate with acrylates and/or methacrylates and copolymers of acrylates and/or methacrylates with vinyl chloride may be added to the cellulosic binder solution in order to obtain fabrics having various desired properties.

Referring now to FIGS. 2 and 3 of the drawing, illustrated therein is an embodiment of the water dispersible nonwoven fabric of this invention as used with a sanitary napkin 20.

Napkin 20 comprises an absorbent core which is contacted by a fluid-pervious cover 26 comprising the bonded nonwoven fabric of this invention. The absorbent core comprises a pad 22 of absorbent fibrous material such as comminuted wood pulp fibers, cotton linters, rayon fibers, cotton staple, bleached sulfite linters, other cellulosic or modified cellulosic fibers and the like. The absorbent core further comprises a fluid-impervious element or barrier means 24 which, for example, may be a thin polyethylene sheet or any other suitable material. As best seen in FIG. 3, barrier means 24 overlies the sides and the bottom surface of absorbent pad 22 (the bottom surface being that portion worn away from the body). Fluid-pervious cover 26 surrounds absorbent pad 22 and barrier means 24 with the lateral edges thereof overlapped and secured on the bottom surface of napkin 20. Cover 26 is extended beyond the ends of the absorbent core to form the usual attachment tabs 28. While FIGS. 2 and 3 illustrate a tabbed napkin, it will be understood by one skilled in the art that the advantages accruing to the use of the nonwoven fabrics of this invention are equally applicable to a tabless product, e.g., one where tabs are not used as attachment means and other attachment means such as, for example, adhesive means, are used. It will also be understood that the absorbent core may comprise, in addition to the absorbent pad and barrier means, a fluid-pervious element such as gauze, tissue, plastic netting and the like if increased strength and/or dimensional stability are desired. It will be further understood that the fluid pervious cover of this invention need not completely surround the absorbent pad as illustrated in FIGS. 2 and 3. For example, one could provide a fluid pervious cover, the edges of which are adhered to the edges of the barrier means; in such a case, the barrier means and fluid pervious cover would cooperate to form an enclosure for the pad of absorbent fibrous material.

The nonwoven fabric of this invention is uniquely suited to serve as a fluid-pervious covering in a sanitary napkin, such as shown in FIGS. 2 and 3, because it is resistant to abrasion and exhibits satisfactory tensile strength when it has been dampened or wetted with menstrual fluid, which has a salt content of about 0.8 percent to about 1.5 percent by weight. The fabrics of this invention are resistant to solutions containing more than about 0.8 percent salt, but are completely dispersible when introduced into water. It will be apparent that, by employing a water-dispersible material for the barrier means and a water-dispersible absorbent pad, the sanitary napkin of FIGS. 2 and 3 may be conveniently and completely disposed of by flushing through a water closet.

Alternatively, the illustrated napkin may be provided with a non-water dispersible barrier means and a water-dispersible absorbent pad. In that case, fluid-pervious covering 26 is first removed and the barrier means is separated from the pad; the pad and covering can then be dropped into a water closet for disposal. In either case, the unique nonwoven fabric of this invention will be completely dispersed in a water closet under the swirling action of the water supplied thereto and will not impair the normal operation of the water closet and associated plumbing.

Referring to FIGS. 4 and 5 of the drawing, there is illustrated therein another embodiment of the water dispersible nonwoven fabric of this invention as used with a disposable diaper 30.

Diaper 30 comprises an absorbent core and a fluid-pervious facing 36 comprising the nonwoven fabric of this invention. The absorbent core comprises an absorbent layer 32 of fibrous material such as comminuted wood pulp fibers, cotton linters, rayon fibers, cotton staple, bleached sulfite linters, other cellulosic or modified cellulosic fibers, and the like. The absorbent core further comprises a body fluid-impervious element or barrier means 34 which overlies the bottom surface of absorbent layer 32. Barrier means 34 may comprise for example, a thin sheet of polyethylene or other suitable material. Where barrier means 34 is not water-dispersible, it is convenient that it be easily removed from the remainder of the diaper so as to minimize disposal problems. Fluid-pervious facing 36 overlies the top surface of absorbent layer 32. In the embodiment illustrated in FIGS. 4 and 5, it will be observed that barrier means 34 and fluid-pervious facing 36 are substantially coextensive and are joined together at their peripheries 38 by methods well known in the art such as adhesive bonding, stitching, and heat sealing techniques.

While FIG. 4 illustrates a disposable diaper having a particular construction, it will be recognized by those skilled in the art that the advantages accruing to the use of the nonwoven fabrics of this invention are equally applicable to disposable diapers having other, widely varying constructions. The absorbent core is not limited to the structure illustrated, but may include a fluid-pervious element, such as gauze, tissue, plastic netting and the like, if it is desired to increase strength and/or structural integrity.

The nonwoven fabric of this invention is uniquely suited to serve as the fluid-pervious facing of a disposable diaper as shown in FIG. 4 because it is resistant to abrasion and exhibits acceptable tensile strength when dampened or wetted with urine. Urine, as in the case of menstrual fluid, has a salt content of about 0.8% to about 1.5% by weight. As already indicated, the nonwoven fabrics herein are resistant to solutions containing about 0.8% or more by weight of sodium chloride. It will be apparent that by employing a water-dispersible material for the barrier means and a water-dispersible, absorbent layer, the diaper of FIG. 4 can be safely and conveniently disposed of by flushing through a water closet. When the diaper of FIG. 4 has been provided with a barrier sheet that is not water dispersible, but has a water-dispersible, absorbent layer, then the layer and the facing may be safely flushed after they have been separated from the barrier means.

Those skilled in the art will readily understand that the water-dispersible nonwoven fabric of this invention may be advantageously employed in the preparation of a wide variety of absorbent products designed to be contacted with body fluids. Many such absorbent products need only comprise a core of absorbent material in combination with said nonwoven fabric. For example, an absorbent surgical dressing could be made comprising a relatively thin, rectangular layer of absorbent material with the nonwoven fabric overlying one or more sides thereof. Similarly, as in the case of a tampon, the nonwoven fabric could overlie a cylindrical core of absorbent material. Alternatively, the core of absorbent material could be in the form of a sphere, a cube, a disc, or other desirable geometrical configuration.

In order to better illustrate the invention, the following examples are given:

EXAMPLE 1

This Example describes the preparation of a water dispersible, salt solution insoluble cellulose ester sulfate resin according to a process which comprises slurrying the cellulose (in the form of woodpulp) in an inert organic liquid, sulfating the cellulose by reacting the cellulosic slurry with a sulfating mixture comprising an alkali acetyl sulfate, esterifying the sulfated cellulose in a reaction mixture comprising the inert organic liquid, sulfated cellulose and an acylating agent and precipitating the desired alkali salt of the sulfated cellulose ester from solution in said reaction mixture by combining said reaction mixture with an aqueous precipitation medium maintained at a specified pH range.

400 grams of woodpulp (ITT Rayoniers Placetate-F) was ground and added to 2000 grams of glacial acetic acid to form a slurry which was tumbled in a closed cylindrical reactor for 20.5 hours at 24° C.

A sulfating mixture comprising sodium acetyl sulfate was prepared as follows: 162.9 grams acetic anhydride and 52.5 grams glacial acetic acid were added to a 1 liter jacketed resin flask. 30.8 grams of sodium sulfate were added and the contents stirred for 5 minutes. 20.15 grams of concentrated sulfuric acid (98% by weight) were added dropwise at such a rate that the temperature of the reactor contents did not exceed 55° C. The rate of addition of sulfuric acid may be increased, if desired, if cooling is applied by circulating ice water through the jacket of the reactor. The reactor was stirred for 30 minutes after the addition of the sulfuric acid was completed.

The slurry of woodpulp in glacial acetic acid was transferred to a jacketed, double planetary mixer (Ross reactor) equipped with a thermometer and a stirrer and was cooled to 18° C. The sulfating mixture was added to the Ross reactor at a rate such that the temperature of the contents did not exceed 32° C. The use of external cooling permits faster addition of the sulfating mixture. Stirring was continued for 30 minutes after the addition of the sulfating mixture has been completed. 112.0 grams of concentrated sulfuric acid were then added to the Ross reactor at a rate such that the temperature of the contents did not exceed 32° C.

The sulfated cellulose was then acylated by adding 1080 grams of acetic anhydride, pre-cooled to −10° C to the contents of the Ross reactor, the temperature in the reactor being maintained below 32° C during this addition. When the addition of the acetic anhydride was completed, stirring was continued and the temperature of the contents of the Ross reactor was maintained at 32° C, until 2 hours, counting from the time the acetic anhydride addition was begun, had elapsed.

In order to precipitate the sodium cellulose acetate sulfate from solution in the reaction mixture, the reaction mixture was added to an aqueous precipitation medium comprising 6000 mls. of water, cooled to 5° C. The pH of the aqueous precipitation medium was maintained at a pH of 5.3 during the precipitation procedure by simultaneously adding a 50% by weight solution of aqueous sodium hydroxide. The aqueous precipitation medium was stirred and cooled during the addition of the sodium hydroxide solution and the reaction mixture thereto, and the product precipitated in the form of a fine powder. The precipitated resin was recovered from the aqueous precipitation medium by filtering in a Buchner funnel and was dried at 53° C. Taking advantage of the fact that the desired cellulose ester sulfate is substantially less soluble in cold water than hot, the precipitated product, after grinding in a Wiley mill, was washed with 5000 mls. of water cooled to 5° C, after which the product was isolated by filtration. The washing and isolation steps were repeated 4 times. Upon completion of the wash steps, the product was filtered and dried at 53° C.

528.9 grams of sodium cellulose acetate sulfate were recovered. Analysis gave the following results: 3.82% by weight sulfur, corresponding to a degree of substitution of $SO_4^=$ of 0.36; 1.81% by weight sodium; 34.51% by weight acetyl

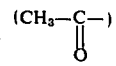

corresponding to a degree of acetyl substitution of 2.40. 6.25 grams of the final product were dissolved in 93.75 g. of a 3:1 weight mixture of acetone and water to form a clear solution. The solution was cast on a piece of silicone release paper and the solvents evaporated. The resulting film was translucent and had good flexibility.

EXAMPLE 2

A second sample of sodium cellulose acetate sulfate was prepared as follows:

400 grams of woodpulp (ITT Rayoniers Placetate-F) were ground, added to 2000 grams of glacial acetic acid, and tumbled in a closed cylindrical reactor for 20.5 hours at 24° C. The resulting slurry was transferred to a jacketed Ross reactor equipped with suitable stirring means. The following reagents were then added, with stirring, to the reactor in the following order: 1297.0 grams of acetic anhydride; 70.0 grams glacial acetic acid; 41.1 grams $Na_2SO_4$; and 146.9 grams of sulfuric acid (98% by weight). Cooling was applied during the above additions so that the temperature in the reactor did not exceed 32° C. Stirring was continued at 32° C for 2 hours, counting from the time the acetic anhydride was added to the reactor. The resulting product was precipitated at pH 5.2 using the precipitation method of Example 1. The resin was then purified and dried as in Example 1.

The resulting resin had the following analysis: 4.08% by weight sulfur; 2.92% by weight sodium; and 34.2% by weight acetyl, degree of sulfate substitution = 0.39; degree of acetyl substitution = 2.40; degree of hydroxyl substitution = 0.22.

EXAMPLE 3

A third sample of sodium cellulose acetate sulfate was prepared as follows:

An "Activated cellulose mixture" was prepared by slurrying 100 grams of ground woodpulp (ITT Rayoniers Placetate-F) in 2350 grams of water at room temperature. The aqueous slurry was stirred for 2 minutes, after which excess water was removed by filtration, leaving behind a total of 271.4 grams of damp woodpulp. The damp woodpulp was then slurried in 500 grams of glacial acetic acid and stirred for 2 minutes. Excess liquid was removed by filtration, leaving 334.1 grams of wet woodpulp behind. The latter was slurried in a mixture of 487 grams of acetic anhydride and 500 grams of glacial acetic acid and stirred for 2 minutes. Excess liquid was filtered from the slurry, leaving an "activated cellulose mixture" comprising 100 grams of woodpulp and 262.2 grams of an acetic acid/acetic anhydride mixture.

A sulfating mixture was then prepared in a jacketed, one liter reactor equipped with a thermometer and stirring means. 234 grams of acetic anhydride (precooled to 5°C) was added to the reactor. 66.7 grams of 98% by weight sulfuric acid was then added at a rate such thhat the temperature in the reactor did not exceed 55°C. External cooling may be applied to the reactor if it is desired to increase the rate of addition of the sulfuric acid. The reactor contents were cooled to 0° C, after which 60 grams of sodium acetate were added. The contents of the reactor were then stirred until the sodium acetate was completely dissolved.

The above mentioned "activated cellulose mixture" was transferred to a stirred 5 liter, jacketed reactor containing 2200 grams of glacial acetic acid.

The above described sulfating mixture was slowly added to the reactor, cooling being applied to insure that the temperature in the reactor did not exceed 32° C. Stirring was continued for 30 minutes after all of the sulfating mixture had been so added. The temperature in the reactor was maintained at 16° C±1° C during the latter 30 minute stirring period.

The desired product, at this point dissolved in the reaction medium, was precipitated by adding it, with stirring, to 4200 grams of an aqueous precipitation medium comprising 10% by weight each of sodium chloride and sodium hydroxide. During this precipitation step, the pH of the aqueous precipitation medium was maintained at about 6 to 7 by adding thereto, at appropriate intervals and in appropriate amounts, a 50% by weight aqueous solution of sodium hydroxide. The product was isolated by filtration and purified by washing three times with water. The product, after purifying and drying at 50° C, was analyzed and found to have a degree of sulfate substitution = 0.61; a degree of acetyl substitution = 0.14; and a degree of hydroxyl substitution = 2.25.

EXAMPLE 4

Binder solutions of the cellulose acetate sulfates of Examples 1, 2, and 3 were prepared by dissolving these resins in a 3:1 weight mixture of acetone and water to give solutions containing 6.25% by weight resin solids. A fibrous web of 1-9/16 inch, 1.5 denier, surgical grade viscose rayon weighing about 1 ounce per square yard was formed by a standard air-laying technique. Nonwoven fabrics were then prepared by spraying 12 inch × 15 inch samples of the fibrous web with the above indicated binder solutions and drying at 72° F for 2 hours. The weight percent binder solids in the resulting nonwoven fabrics are given in Table I.

The resulting nonwoven fabrics, identified as 4A, 4B, and 4C in Table I, were tested for their tensile strength properties after immersion in water, and after immersion in aqueous solutions containing, respectively, 0.9 percent by weight and 2.0 percent by weight sodium chloride.

The following procedure was used for the determination of tensile strengths in tap water and in aqueous salt solutions. The fabric to be tested was equilibrated for 24 hours at 72° F and 65% relative humidity. Three by one inch strips were cut from the fabric, immersed in the desired test solution, removed, drained for 15 seconds, and gently blotted between paper toweling. The test strips were then tested on an Instron tester using a jaw spacing of 2 inches and a pull speed of 2 inches per minute. The tensile strength of the fabric is measured and reported in units of pounds per inch width of fabric (hereinafter, "Lbs./In.").

The results of the tensile strength tests, which are set forth in Table I, show generally that the tensile strength of a given nonwoven fabric increases as the salt content of the solution in which the fabric is immersed is increased. It is also noted that as the degree of sulfate substitution in the cellulosic binder decreases, tensile strength after immersion in water remains at the same general level, or increases slightly, while tensile strength after immersion in each of the salt solutions increases significantly. Nonwoven fabric 4C, bonded with a resin which has a degree of sulfate substitution (0.61) that lies outside the limits set forth in this patent, shows no difference in its tensile strength in water as compared to the tensile strength in salt solutions.

EXAMPLE 5

Six by six inch swatches of the nonwoven fabrics prepared in accordance with Example 4 are placed in approximately 600 mls. of water contained in a standard 1000 ml. beaker. The water is stirred by hand, care being taken not to touch the fabric swatch under test. In every case, the fabric disperses in the water and cannot be removed in a single piece or in a series of pieces from the water.

TABLE I

| Nonwoven Fabric | 4A | 4B | 4C |
|---|---|---|---|
| Binder Resin | Ex. 1 | Ex. 2 | Ex. 3 |
| D.S. (Sulfate) | 0.36 | 0.39 | 0.61 |
| D.S. (Acetyl) | 2.40 | 2.40 | 0.14 |
| D.S. (Hydroxyl) | 0.24 | 0.22 | 2.25 |
| Wt. % Binder in Fabric | 21.2 | 33.8 | 3.6 |
| Dry Tensile (Lb./in.) | 3.6 | 9.8 | 3.7 |
| Wet Tensile-Water (Lb./in.) | | | |
| 30 sec. | 0.13 | 0.10 | 0.03 |
| 1 min. | 0.12 | 0.08 | 0.02 |
| 3 min. | 0.09 | 0.04 | 0.02 |
| 5 min. | 0.10 | 0.05 | 0.03 |
| 10 min. | 0.09 | 0.05 | 0.03 |
| 20 min. | 0.09 | 0.03 | — |
| 30 min. | 0.07 | 0.04 | 0.03 |
| 120 min. | 0.10 | 0 | 0.03 |
| Wet Tensile-0.9% by weight NaCl (lbs./in.) | | | |
| 30 sec. | 0.38 | 0.63 | 0.04 |
| 1 min. | 0.50 | 0.31 | 0.04 |
| 3 min. | 0.26 | 0.30 | 0.04 |
| 5 min. | 0.41 | 0.25 | 0.04 |
| 10 min. | 0.31 | 0.29 | 0.04 |
| 20 min. | 0.38 | 0.34 | — |
| 30 min. | 0.35 | 0.20 | 0.04 |
| 120 min. | 0.28 | 0.23 | 0.04 |
| Wet Tensile-2.0% by weight NaCl (lb./in.) | | | |
| 30 sec. | 0.56 | 0.75 | 0.05 |
| 1 min. | 0.62 | — | 0.05 |
| 3 min. | — | 0.66 | 0.04 |
| 5 min. | 0.66 | 0.51 | 0.04 |
| 10 min. | 0.61 | 0.44 | 0.05 |
| 20 min. | — | 0.63 | — |
| 30 min. | 0.60 | 0.49 | 0.04 |
| 120 min. | — | 0.56 | 0.05 |

D.S. = Degree of Substitution

EXAMPLE 6

Two samples of sodium cellulose acetate sulfates, designated 6A and 6B were prepared by the method described in Example 1 by varying the amounts of the sulfating mixture used and by varying the quantities of acetic anhydride and sulfuric acid comprising the acetylation mixture. The pH maintained during the precipitation step is indicated in Table II. The resulting sodium cellulose acetate sulfate resins had the degrees of substitution of sulfate ($SO_4^=$) and acetyl $$(CH_3-\underset{\underset{O}{\|}}{C}-)$$

groups as shown in Table II.

Resins 6A and 6B are dissolved in 3:1 mixtures by weight of acetone and water to give separate binder solutions containing 30% by weight resin. A fibrous web of 1⅛ inch, denier viscose rayon weighing about one ounce/yd² is formed using a standard carding technique. Nonwoven fabrics are then prepared by spraying swatches of the fibrous web with the respective binder solutions to achieve about 100% wet pick-up of the binder solution. The sprayed webs are then air dried, after which they are heated in a vacuum oven for 15 minutes at 50° C. The resulting nonwoven fabrics are tested for their tensile strength. The tensile strength of the nonwoven fabric having resin 6A (D.S.=0.27) as its binder is found to have a tensile strength after exposure to a 0.9% by weight aqueous solution of sodium chloride that is about 3–5 times its tensile strength after exposure to distilled water; and a tensile strength after exposure to a 2.0% by weight aqueous solution of sodium chloride that is about 8–10 times its tensile strength in distilled water.

TABLE II

| SAMPLE | SULFATING MIXTURE GRAMS USED | | | | ACETYLATING MIXTURE GRAMS USED | | pH of AQUEOUS PRECIPITATION MEDIUM | DEGREES OF SUBSTITUTION | | |
|---|---|---|---|---|---|---|---|---|---|---|
| | (Ac)₂O | HAc | Na₂SO₄ | H₂SO₄(98-%) | (Ac)₂O | H₂SO₄(98%) | | $SO_4^=$ | $CH_3-C\overset{\diagup O}{\diagdown}$ | OH |
| 6A | 162.9 | 52.5 | 30.8 | 20.15 | 1080 | 112 | 5.45 | 0.27 | 2.62 | 0.11 |
| 6B | 122 | 39.4 | 23.1 | 15.1 | 1080 | 60 | 5.2 | 0.15 | 1.97 | 0.88 |

All parts are parts by weight per 400 parts of woodpulp
(Ac)₂O = acetic anhydride; HAc = acetic acid.

The tensile strength of the nonwoven fabric having resin 6B (D.S. = 0.15) as its binder is found to have a tensile strength after exposure to a 0.9% by weight aqueous solution of sodium chloride that is about 4–6 times its tensile strength after exposure to distilled water, and a tensile strength after exposure to a 2.0% by weight aqueous solution of sodium chloride that is about 7–9 times its tensile strength in distilled water.

The two fabrics are tested and found to be dispersible in water, i.e., the dispersed fabric cannot be removed in a single piece or in a series of pieces from the water. It is observed that, other variables being constant, the time required for the fabric to become dispersed in water increases as the degree of sulfate substitution is decreased.

EXAMPLE 7

A disposable diaper is made as follows: An absorbent fibrous layer, measuring about 11 inches by about 15 inches, is prepared from comminuted woodpulp. The absorbent layer, which weighs about 20–25 grams, is then placed on a piece of 1 mil. polyethylene film measuring about 12 inches by about 16 inches. This polyethylene film serves as a backing layer. A piece of nonwoven fabric 4A (Example 4), also measuring about 12 inches by 16 inches, is placed over the absorbent layer in substantially coextensive relationship with the polyethylene film. This nonwoven fabric serves as the facing of the disposable diaper. Nonwoven fabric 4A and the polyethylene film are joined along their peripheries with any suitable adhesive means, for example, an aqueous based polyvinyl acetate adhesive, so that the absorbent layer is confined therebetween. Nonwoven fabric 4A has acceptable strength and good abrasion resistance in the presence of urine. After use, nonwoven fabric 4A and the absorbent layer are separated from the polyethylene film. The nonwoven fabric and the absorbent layer are then easily and safely disposed of by flushing in a toilet. It will be understood that the above example is given for purposes of illustration only. Those skilled in the art will recognize that the polyethylene film could be replaced by other types of film or by any suitable woven orr nonwoven fabric. The absorbent layer may comprise any of the other absorbent materials, for example, cellulose wadding, well known in the art. Additionally, it will be recognized that if the diaper comprises, in addition to the nonwoven fabric of this invention, a flushable absorbent layer and a flushable backing material, then the entire diaper may be disposed of by flushing in a toilet.

What is claimed is:

1. A water-dispersible nonwoven fabric comprising: a layer of overlapping, intersecting fibers, said fibers having a length not more than about 2 inches; and from about 4 to about 35 percent by weight of the fabric of an alkali salt of a sulfated cellulose ester resin binder distributed in said fabric, said resin binder having an average of from about 0.1 to about 0.45 sulfate groups per anhydroglucose unit.

2. A water-dispersible nonwoven fabric according to claim 1, wherein said sulfated cellulose ester resin has an average of from about 0.27 to about 0.40 sulfate groups per anhydroglucose unit.

3. A water dispersible nonwoven fabric according to claim 1, wherein the ester group of said sulfated cellulose ester resin has from 1 to 6 carbon atoms.

4. A water-dispersible nonwoven fabric according to claim 3, wherein said sulfated cellulose ester is sodium cellulose acetate sulfate.

5. A water-dispersible nonwoven fabric according to claim 1 wherein said fibers are viscose rayon fibers.

6. A water-dispersible nonwoven fabric according to claim 1 wherein the length of said fibers does not exceed about one and one half inches.

7. A water-dispersible nonwoven fabric according to claim 1, wherein said resin binder is distributed in said fabric in a predetermined pattern.

8. A water-dispersible nonwoven fabric according to claim 1, wherein said fibers are viscose rayon fibers having a length of from about one half inch to about one and one half inches and said resin binder is sodium cellulose acetate sulfate.

9. A water-dispersible nonwoven fabric according to claim 1, wherein there is from about 4 to about 20 percent of said resin binder by weight of the fabric.

10. A water-dispersible nonwoven fabric according to claim 1 wherein said fibers are woodpulp fibers.

11. A water-dispersible nonwoven fabric comprising: a layer of overlapping, intersecting textile fibers, said fibers being viscose rayon fibers from about ½ inch to about 1½ inches in length and from about 4 percent to about 20 percent of sodium cellulose acetate sulfate distributed in said fabric, said sodium cellulose acetate sulfate having an average of from about 0.27 to about 0.40 sulfate groups per anhydroglucose unit.

12. An absorbent product for contacting body fluids comprising: an absorbent core and a fluid-pervious, water-dispersible nonwoven fabric covering at least a portion of said absorbent core; said nonwoven fabric comprising a layer of overlapping, intersecting fibers, said fibers having a length not more than about 2 inches; and, distributed in said fabric, from about 4 to about 20 percent by weight of the fabric of an alkali cellulose ester sulfate resin binder, said resin binder having an average of from about 0.27 to about 0.40 sulfate groups per anhydroglucose unit.

13. An absorbent product according to claim 12, wherein said absorbent core includes a fluid-pervious element.

14. An absorbent product according to claim 13, wherein the fluid-pervious element is tissue.

15. An absorbent product according to claim 13, wherein the fluid-pervious element is gauze.

16. An absorbent product according to claim 13, wherein the fluid-pervious element is a plastic netting.

17. An absorbent product according to claim 12, wherein said absorbent core includes a fluid-impervious element.

18. An absorbent product according to claim 17, wherein the fluid-impervious element comprises polyethylene.

19. An absorbent product according to claim 12, wherein the absorbent core includes a fluid-pervious element and a fluid-impervious element.

20. An absorbent product according to claim 19, wherein the fluid-pervious element is tissue and the fluid-impervious material comprises polyethylene.

* * * * *